(12) United States Patent
Wisniewski et al.

(10) Patent No.: US 12,371,233 B2
(45) Date of Patent: Jul. 29, 2025

(54) VALVE

(71) Applicant: AptarGroup, Inc., Crystal Lake, IL (US)

(72) Inventors: John Wisniewski, Wauwatosa, WI (US); Robert LaBean, Freeland, MI (US)

(73) Assignee: AptarGroup, Inc., Crystal Lake, IL (US)

( * ) Notice: Subject to any disclaimer, the term of this patent is extended or adjusted under 35 U.S.C. 154(b) by 303 days.

(21) Appl. No.: 18/025,423

(22) PCT Filed: Sep. 30, 2021

(86) PCT No.: PCT/US2021/052885
§ 371 (c)(1),
(2) Date: Mar. 9, 2023

(87) PCT Pub. No.: WO2022/086691
PCT Pub. Date: Apr. 28, 2022

(65) Prior Publication Data
US 2023/0348154 A1 Nov. 2, 2023

Related U.S. Application Data

(60) Provisional application No. 63/093,514, filed on Oct. 19, 2020.

(51) Int. Cl.
*B65D 47/20* (2006.01)
*A61M 39/24* (2006.01)

(52) U.S. Cl.
CPC ......... *B65D 47/2081* (2013.01); *A61M 39/24* (2013.01); *A61M 2039/2433* (2013.01)

(58) Field of Classification Search
CPC .. B65D 47/2081; B65D 43/164; A61M 39/24; A61M 2039/2433; A61M 2039/242
See application file for complete search history.

(56) References Cited

U.S. PATENT DOCUMENTS

| 1,709,948 A | 4/1929 | Proctor |
| 1,880,103 A | 9/1932 | Murdoch |

(Continued)

FOREIGN PATENT DOCUMENTS

| DE | 1486228 B1 * | 5/1971 |
| DE | 2704164 A1 * | 8/1978 |

(Continued)

*Primary Examiner* — Bob Zadeh
(74) *Attorney, Agent, or Firm* — Wood, Phillips, Katz, Clark & Mortimer

(57) ABSTRACT

A valve (100) includes a base (110) defining a central axis (114). The valve (100) includes a post (118) connected to the base (110) and extending axially outwardly from the base (110), in the direction along the central axis (114). The valve (100) includes at least one flow aperture (122) in one or both of the base (110) and/or the post (118). The valve (100) further includes a flexible membrane (126) having an orifice (130) and having a non-dispensing configuration wherein the orifice (130) is located proximate to the post (118) to minimize communication through the valve (100). The flexible membrane (126) has a dispensing configuration wherein the orifice (130) is moved away from the post (118) for establishing communication through the valve (100).

24 Claims, 8 Drawing Sheets

(56) References Cited

U.S. PATENT DOCUMENTS

| | | | |
|---|---|---|---|
| 1,925,926 A | 9/1933 | Kunkel | |
| 1,987,156 A | 1/1935 | Paparello | |
| 3,977,577 A | 8/1976 | Nilson | |
| 4,141,474 A | 2/1979 | Nilson | |
| 4,141,475 A * | 2/1979 | Nilson | B65D 47/2081 222/548 |
| 4,349,134 A | 9/1982 | Schuster et al. | |
| 4,474,314 A * | 10/1984 | Roggenburg, Jr. | B65D 47/2081 222/521 |
| 4,699,300 A | 10/1987 | Blake | |
| 4,739,906 A * | 4/1988 | LoTurco | B65D 47/2081 222/484 |
| 4,798,311 A | 1/1989 | Workum | |
| 5,388,615 A | 2/1995 | Edlund et al. | |
| 5,692,651 A | 12/1997 | Fuchs | |
| 6,145,707 A | 11/2000 | Baudin | |
| 6,244,476 B1 * | 6/2001 | Moretti | B65D 47/242 222/521 |
| 6,543,652 B1 | 4/2003 | Kelder et al. | |
| 6,616,012 B2 | 9/2003 | Dark | |
| 6,749,092 B2 * | 6/2004 | Olechowski | B65D 47/2031 222/525 |
| 6,840,410 B2 | 1/2005 | Dark | |
| 6,889,876 B2 | 5/2005 | Markert | |
| 6,938,794 B2 | 9/2005 | Elder | |
| 7,152,763 B2 | 12/2006 | Stull et al. | |
| 7,195,138 B2 | 3/2007 | Foster et al. | |
| 7,255,250 B2 | 8/2007 | Pugne | |
| 7,299,952 B2 | 11/2007 | Stull et al. | |
| 7,503,469 B2 | 3/2009 | Bloom et al. | |
| 7,681,750 B2 | 3/2010 | Jackel | |
| 7,731,066 B2 | 6/2010 | Norris et al. | |
| 8,220,670 B2 | 7/2012 | Moribata et al. | |
| 8,397,957 B2 | 3/2013 | Bloom et al. | |
| 8,397,958 B2 | 3/2013 | Smith et al. | |
| 8,413,830 B2 | 4/2013 | Guglielmini | |
| 8,608,034 B2 | 12/2013 | Bloom | |
| 8,640,928 B2 | 2/2014 | Ellenkamp-Van Olst et al. | |
| 8,794,489 B2 | 8/2014 | Bloom et al. | |
| 8,820,591 B2 | 9/2014 | Smith et al. | |
| 9,340,335 B2 | 5/2016 | Ellenkamp-Van Olst et al. | |
| 9,604,836 B2 | 3/2017 | Nini | |
| 9,630,829 B2 | 4/2017 | Sokol | |
| 9,757,749 B2 | 9/2017 | Bloc | |
| 10,000,316 B2 | 6/2018 | Geiger et al. | |
| 10,259,623 B2 | 4/2019 | Bull | |
| 10,350,620 B2 | 7/2019 | Knight | |
| 10,450,113 B2 | 10/2019 | Kieras et al. | |
| 10,518,943 B2 | 12/2019 | Gelov et al. | |
| 10,723,527 B2 * | 7/2020 | Knight | F16K 15/147 |
| 2001/0052531 A1 * | 12/2001 | Randall | B65D 47/0809 222/521 |
| 2004/0112920 A1 | 6/2004 | Felten et al. | |
| 2004/0251278 A1 | 12/2004 | Arai | |
| 2005/0087571 A1 | 4/2005 | Dark | |
| 2006/0261097 A1 | 11/2006 | Bailey | |
| 2010/0102021 A1 | 4/2010 | Guglielmini et al. | |
| 2010/0126954 A1 * | 5/2010 | Nilsson | B65D 47/36 215/40 |
| 2012/0006860 A1 | 1/2012 | Suffa et al. | |
| 2012/0024913 A1 | 2/2012 | Suffa et al. | |
| 2012/0067922 A1 | 3/2012 | Benoit-Gonin | |
| 2012/0080450 A1 | 4/2012 | Dziersk et al. | |
| 2013/0161327 A1 | 6/2013 | Lepage et al. | |
| 2017/0183134 A1 | 6/2017 | Bull | |
| 2017/0234446 A1 | 8/2017 | Maloney et al. | |
| 2019/0031406 A1 | 1/2019 | Crawley | |
| 2019/0283055 A1 | 9/2019 | Knight | |
| 2023/0348154 A1 * | 11/2023 | Wisniewski | B65D 47/2081 |

FOREIGN PATENT DOCUMENTS

| | | | |
|---|---|---|---|
| EP | 0046464 A1 | 5/1984 | |
| EP | 0388828 A1 | 9/1990 | |
| EP | 0473994 A2 | 3/1992 | |
| EP | 0505611 A2 | 9/1992 | |
| EP | 1614636 B1 | 1/2008 | |
| EP | 2881334 B1 | 10/2016 | |
| FR | 2758127 A1 * | 7/1998 | B65D 47/2081 |
| GB | 1583494 A * | 1/1981 | |
| SU | 433314 A | 6/1974 | |
| WO | 1982000128 A1 | 1/1982 | |
| WO | 1995026306 A1 | 10/1995 | |
| WO | WO-0021851 A1 * | 1/1999 | B65D 47/2081 |
| WO | 1999064313 A1 | 12/1999 | |
| WO | 2000006460 A1 | 2/2000 | |
| WO | 2000021851 A1 | 4/2000 | |
| WO | 2004076308 A1 | 9/2004 | |
| WO | 2008154754 A1 | 12/2008 | |
| WO | 2018200662 A1 | 11/2018 | |

* cited by examiner

VALVE

PRIORITY

This application claims priority of U.S. Provisional Patent Application No. 63/093,514, filed Oct. 19, 2021, the entire contents of which is incorporated herein by reference.

TECHNICAL FIELD

The present invention relates generally to a valve for dispensing a fluent substance from a container.

BACKGROUND OF THE INVENTION AND TECHNICAL PROBLEMS POSED BY THE PRIOR ART

Valves can be mounted at an opening or port of a closure for a container of a fluent substance, or alternatively mounted within a container or conduit for a fluent substance. Such valves typically have a single slit or have multiple slits through the flexible, resilient valve material to define a normally closed orifice in an initially closed configuration or condition. The orifice opens to permit flow therethrough in response to either a sufficient pressure differential acting across opposite sides of the valve, or in response to mechanical engagement by a sufficiently rigid article such as a probe or cannula inserted through the valve. Such valves that open in response to a sufficiently high pressure differential acting between the opposite sides of the valve are typically designed so that they automatically close to seal or shut off flow therethrough in response to a sufficient reduction of the pressure differential acting across the valve. Similarly, mechanically engageable valves are typically designed so that they automatically close to seal or shut off flow therethrough upon removal of the engaging article.

Forms of such types of valves are disclosed in U.S. Pat. Nos. 5,839,614 and 8,678,249. The descriptions of those patents are incorporated herein by reference thereto to the extent pertinent and to the extent not inconsistent herewith.

Such prior art, conventional valves may be suitable for use with fluent substances, such as liquids and gases, including, inter alia, food products, beverages, lotions, and creams. Such valves are typically molded as a unitary structure (i.e., one-piece structure) from a single substance or material which is flexible, pliable, somewhat elastic, and resilient. This can include elastomers, such as a synthetic, thermosetting polymer, including silicone rubber, such as the silicone rubber sold by Dow Corning Corporation in the United States of America under the trade designation D.C. 99-595 and RBL-9595-40. Another suitable silicone rubber material is sold in the United States of America under the designation Wacker 3003-40 by Wacker Silicone Company.

The conventional valve has a first side surface and a second side surface. In one known application, the first side surface faces an interior of a fluent substance container and the second side surface faces an exterior, ambient environment.

The conventional valve has a peripheral attachment portion or mounting flange for being mounted or attached to a container of a fluent substance. Typically, this may be achieved through a retention structure or ring that can mate with a feature on the closure or container on which the valve may be installed.

The inventors of the present invention have discovered that, at least in some applications, a conventional valve may not be suitable for some containers of fluent substances or that the conventional valve requiring a separate retainer ring may be cost prohibitive.

The inventors of the present invention have determined that for at least some applications in which some types of fluent substances are contained within a package or container, it may be desirable to provide an improved valve that can eliminate, or at least reduce or minimize, undesirable, premature valve opening events and/or ingress or egress leakage events during shipping and/or handling of the container upon which the valve is installed.

The inventors of the present invention have also determined that it would be desirable to provide, at least for one or more types of applications, an improved valve that can be configured for use with a fluent substance container so as to have one or more of the following advantages compared to conventional slit-type silicone valves (1) ease of manufacture and/or assembly, (2) relatively low cost of manufacture and/or assembly, and (3) accommodation of the manufacture of the valve by means of efficient, high-quality, large-volume techniques with a reduced product reject rate to produce valves with consistent operating characteristics.

The inventors of the present invention have discovered how to provide such a valve that includes novel, advantageous features not heretofore taught or contemplated by the prior art, and which can accommodate designs having one or more of the above-discussed benefits or features.

BRIEF SUMMARY OF THE INVENTION

The inventors of the present invention have discovered how to provide an improved lower cost valve system for permitting selective communication through the valve (from one side to the other) to accommodate flow of a fluent substance therethrough. The valve may be assembled with, or provided within, a package or container of a fluent substance, or a fluid handling system (such as a fluent substance dispensing system), that has an opening between the exterior and interior of the container or system at which the valve can be installed.

According to one broad aspect of the invention, the valve includes a base defining a central axis, and a post connected to the base and extending axially outwardly from the base, in the direction along the central axis. The valve includes at least one flow aperture that may be formed in one or both of the base and/or the post. The valve further includes a flexible membrane defining an orifice and a non-dispensing configuration wherein the orifice is located proximate to the post to minimize, or at least restrict, communication of a fluent substance through the valve. The flexible membrane has a dispensing configuration wherein the orifice is moved away from the non-dispensing configuration proximate to the post for establishing or permitting a substantial communication of a fluent substance through the valve.

According to one aspect of the invention, the valve is formed as a unitary construction, preferably from a single thermoplastic elastomer for being installed in either a closure for a container or directly in the container without the need for any retaining ring or adhesive.

According to one aspect of the invention, the base and the flexible membrane are connected by a hinge. Preferably, the base and the flexible membrane have a generally planar, as-molded configuration, wherein the flexible membrane is configured to be rotated about the hinge away from the generally planar, as-molded configuration into the non-dispensing configuration such that the orifice is located around the post. Preferably, the orifice of the flexible membrane is circular.

In another aspect of the invention, the least one flow aperture has the form of a pair of diametrically opposing flow apertures extending through each of the base and the post.

In yet another aspect of the invention, the post is generally cylindrical and terminates in a distal end. Preferably, the distal end extends axially outwardly of the flexible membrane in the non-dispensing configuration, relative to the central axis. According to one preferred embodiment, the post terminates in a distal end having a frustoconical cross-sectional shape, when viewed in a vertical plane containing the central axis. In another embodiment, the post terminates in a substantially flat distal end.

According to one aspect of the invention, the flexible membrane includes a peripheral wall for sealing against a portion of the base and a transverse wall extending laterally inwardly of the peripheral wall and defining the orifice. Preferably, the peripheral wall defines a top end and a bottom end, wherein the transverse wall extends from the bottom end and is located axially inwardly (toward the container interior along the central axis) of the top end with the flexible membrane in the non-dispensing (i.e., ready to dispense) configuration. Still more preferably, the transverse wall is substantially flat with the flexible membrane in the non-dispensing configuration.

In another form of the present invention, the base includes an outer wall surrounding the post and an inner wall extending laterally inwardly from the outer wall. Preferably, the flexible membrane includes a peripheral wall for sealing against the outer wall of the base and a transverse wall extending laterally inwardly of the peripheral wall and defining the orifice. According to one preferred form, the peripheral wall includes at least one annular projection or other frictional means for maintaining the flexible membrane in the non-dispensing configuration relative to the base. Preferably, the outer wall includes a flange extending laterally outwardly therefrom for securing the base with a closure or a container. Preferably, the valve is arranged in the closure at a location that is axially inward of an opening of the closure.

In the preferred form of the invention, the flexible membrane does not contact, and is spaced laterally from, a lateral surface of the post with the flexible membrane in the non-dispensing configuration.

In another form of the invention, the flexible membrane seals against a lateral surface of the post with the flexible membrane the non-dispensing configuration.

According to yet another form of the invention, the flexible membrane does not contact, and is spaced axially outwardly from, a distal end of the post with the flexible membrane in the non-dispensing configuration.

In another form of the present invention, the flexible membrane seals axially against a distal end of the post with the flexible membrane in the non-dispensing configuration.

In still another form of the present invention, the flexible membrane is resilient and configured to move from the dispensing configuration to the non-dispensing configuration when the flexible membrane is subjected to a pressure differential below a predetermined threshold.

According to another form of the invention, the flexible membrane further has an in-venting configuration wherein the flexible membrane is movable axially inwardly from the non-dispensing configuration to permit an inflow of air through the valve.

According to one broad form of the present invention, the valve includes a base defining a central axis, a post connected to the base, at least one flow aperture in the base and/or the post, and a flexible membrane. The membrane includes an orifice having a non-dispensing configuration wherein the orifice is located proximate to the post to minimize or inhibit communication of a fluent substance through the valve. The membrane defines a dispensing configuration wherein the orifice is moved away from the post for establishing communication of a fluent substance through the valve. The base, the post, and the membrane are a unitary structure.

According to another broad form of the present invention, the valve includes a base defining a central axis, a post connected to the base, at least one flow aperture in the base and/or the post, and a flexible membrane. The membrane includes an orifice having a non-dispensing configuration wherein the orifice is located proximate to the post to minimize or inhibit communication of a fluent substance through the valve. The membrane defines a dispensing configuration wherein the orifice is moved away from the post for establishing communication of a fluent substance through the valve. The base and the membrane are each separately formed structures.

According to still another broad form of the present invention, the valve includes a base defining a central axis, a post connected to the base, at least one flow aperture in the base and/or the post, and a flexible membrane. The membrane includes an orifice having a non-dispensing configuration wherein the orifice is located proximate to the post to minimize or inhibit communication of a fluent substance through the valve. The membrane defines a dispensing configuration wherein the orifice is moved away from the post for establishing communication of a fluent substance through the valve. The flexible membrane has an in-venting configuration wherein the flexible membrane is moved inwardly from the non-dispensing configuration to permit an inflow of air through the valve.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same, FIG. 1 shows the valve in an unstressed, as-manufactured, open configuration prior to being rearranged into an operative configuration;

FIG. 11 illustrates the valve installed at the top end of a closure body for being located at the opening of a container of a fluent substance.

DESCRIPTION OF THE PREFERRED EMBODIMENTS

While the valve of the present invention is susceptible of embodiment in many different forms, this specification and the accompanying drawings disclose only some specific forms as examples of the invention. The invention is not intended to be limited to the embodiments so described, however.

Figure 10:
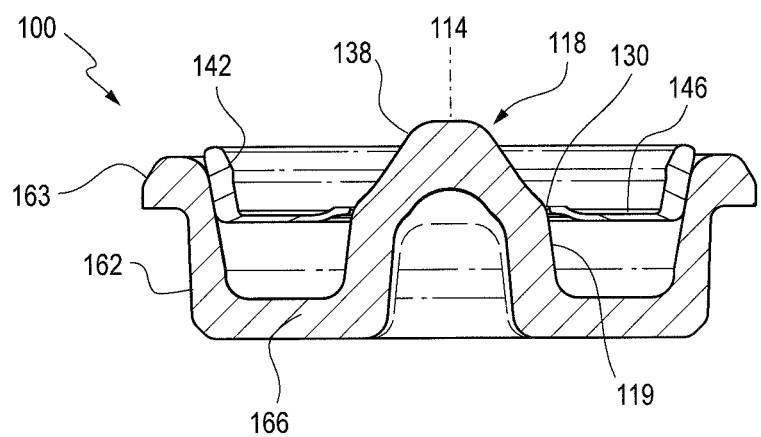
FIG. 10 is a cross-sectional view of the valve of FIG. 7, taken along view plane 10-10 in FIG. 9.

For ease of description, the valve of this invention is described, with reference to the drawings, in a generally horizontal orientation that the valve could have when installed on an upright fluent substance container or system. The terms "axial", "radial", and "lateral" are used herein with respect to a central axis (114 in FIGS. 5 and 10), generally defined by the center of the valve base or body. As employed herein, the phrase "axially outwardly" refers to the direction upwardly in the figures, along the axis 114 away from the interior of a container on which the valve could be installed (i.e., in the dispensing direction). The phrase "axially inwardly" refers to the direction downwardly in the figures, along the axis 114 toward the interior of a container on which the valve could be installed (i.e., in the in-venting direction). As employed herein, the phrase "radially inwardly" refers to a direction normal to, and moving toward, the axis 114. The phrase "radially outwardly" refers to a direction normal to, and moving away from, the axis 114. The phrase "laterally outwardly" refers to a direction away from the axis 114 and also within a plane that is normal to the axis 114. The phrase "laterally inwardly" refers to a direction toward the axis 114 and also within a plane that is normal to the axis 114. It will be understood, however, that this invention may be manufactured, stored, transported, used, or sold in orientations other than the orientation shown.

The valve of this invention is suitable for use with a variety of conventional or special fluent substance containers or systems (e.g., fluent substance handling or processing systems, dispensing systems, etc.) having various designs, the details of which, although not illustrated or described, would be apparent to those having skill in the art and an understanding of such systems.

FIGS. 1-12 illustrate a first embodiment of a valve 100 according to the present invention. The valve 100 is used for selectively permitting communication through the valve 100 from one side of the valve to the other side (e.g., into or out of a fluent substance container or handling or dispensing system, conduit, or package), and the valve 100 typically would be in communication with an interior of such a container or system. The valve 100 is especially adapted to be installed within a closure 200 (FIG. 11 only) for being installed at an opening of a container for a fluent substance dispensing system (not illustrated).

The fluent substance container may be, for example, a flexible bag or a rigid bottle. The valve 100 could also be installed on a reservoir, a fluent substance processing system, or a fluent substance dispensing system, which contains a fluent substance at ambient atmospheric pressure or above ambient atmospheric pressure (including a system in which the pressure results from the static head of the fluent substance within the system and/or in which the system generates or otherwise creates a pressurized fluent substance therein).

The first illustrated embodiment of the valve 100 is flexible, resilient, pressure-openable, and self-closing and is intended for applications currently served by prior art slit-type valves. Forms of prior art slit-type valves are disclosed in the U.S. Pat. Nos. 8,678,249 and 5,839,614. The descriptions of those patents are incorporated herein by reference thereto to the extent pertinent and to the extent not inconsistent herewith.

The valve 100 is suitable for use with fluent substances, such as liquids including, beverages, food products, lotions, and creams. The valve 100 is preferably molded as a unitary structure (i.e., one-piece structure) from a material which is flexible, pliable, elastic, and resilient. This can include elastomers, such as a synthetic, thermoplastic elastomers (TPE).

The valve 100 could be molded from thermosetting materials or from thermoplastic propylene, ethylene, urethane, and styrene, including their halogenated counterparts, etc. For example, a particular non-silicone material that may be employed is ethylene propylene diene monomer rubber ("EPDM"). Another non-silicone material that may be employed is nitrile rubber. It is desirable in many applications that the material be substantially inert so as to avoid reaction with, and/or adulteration of, the fluent substance that will come into contact with the valve 100.

While the valve 100 is illustrated as being formed from a material as a single substance that defines a unitary layer of material substance, it will be appreciated that for some applications the valve 100 may be formed from a material that is defined by two or more layers of different substances. For example, one layer of the valve 100 material may be formed form a silicone rubber and one or more other layers of the valve 100 material may be formed from coatings or laminations of one or more different substances.

Figure 1:
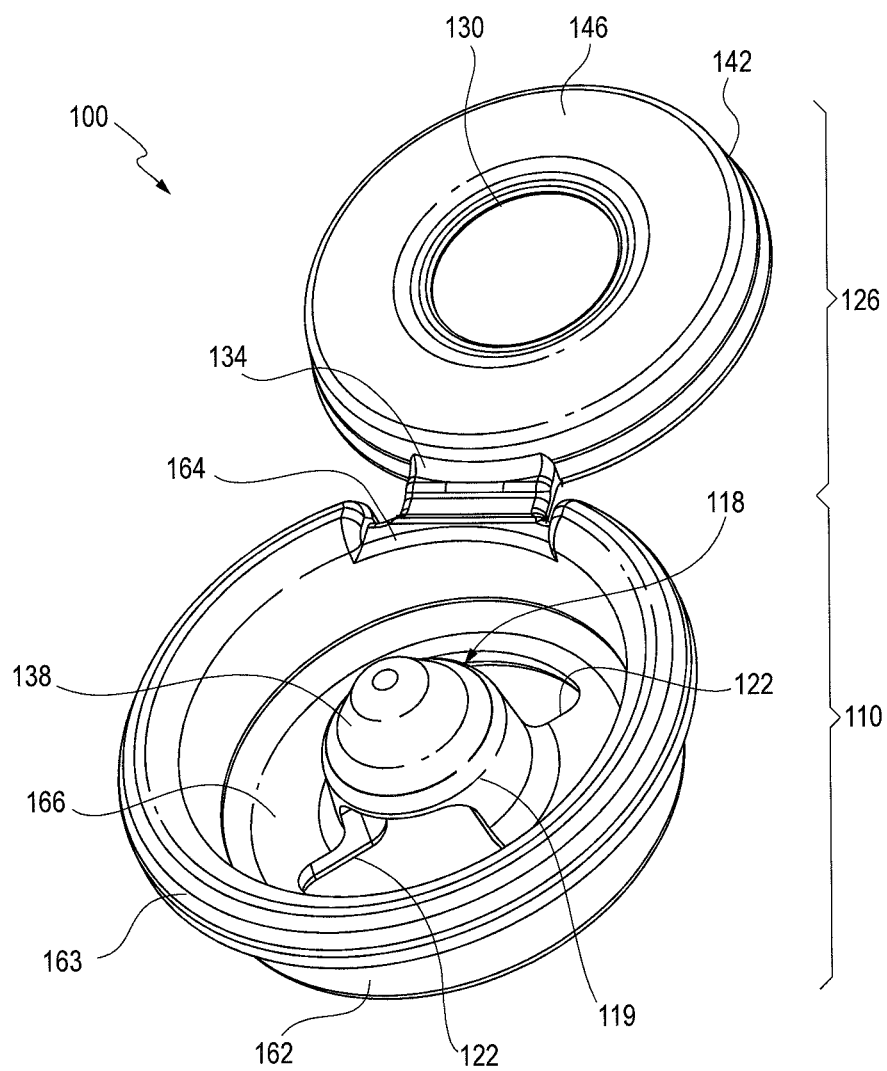
FIG. 1 is an enlarged, isometric view, taken from above, of a valve according to the present invention.
Figure 4:
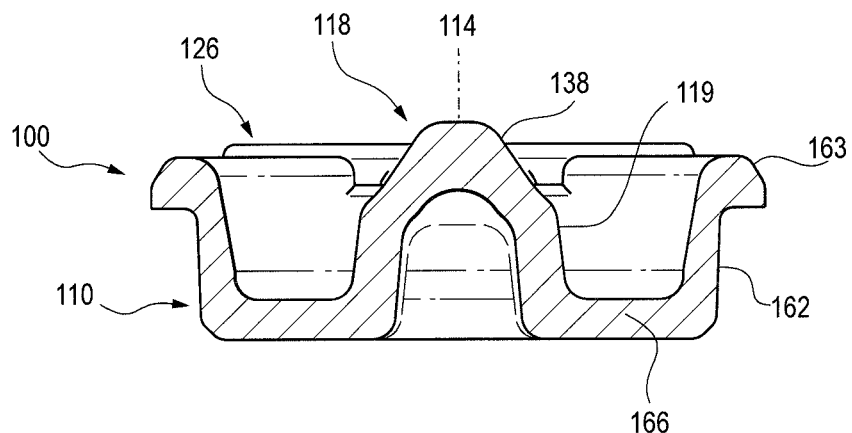
FIG. 4 is a cross-sectional view of the valve of FIG. 1, taken along view plane 4-4 in FIG. 3.
Figure 5:
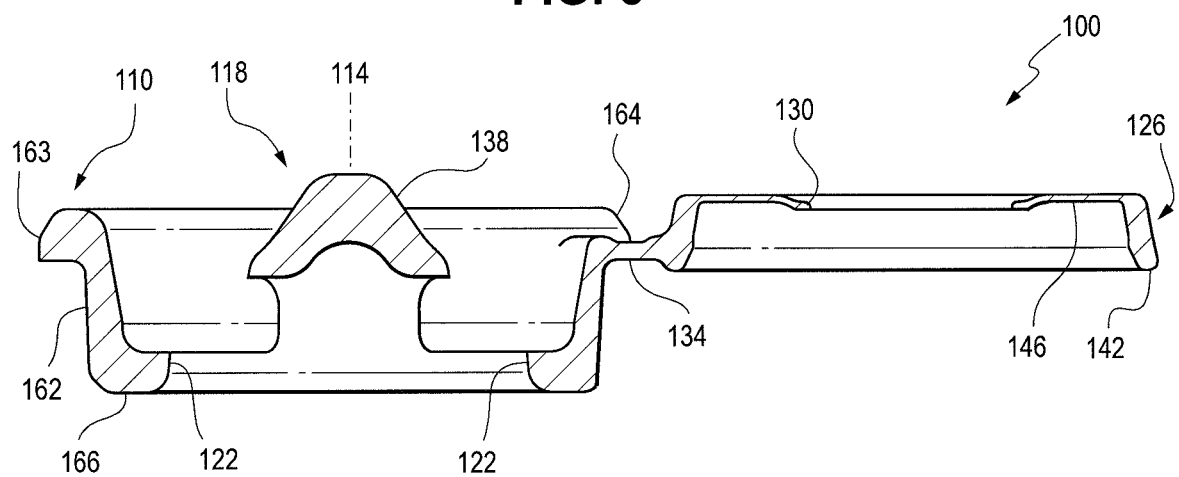
FIG. 5 is a cross-sectional view of the valve of FIG. 1, taken along view plane 5-5 in FIG. 3.

With reference to FIGS. 1 and 5, the valve 100 has the basic components of a body or base 110 defining the central axis 114 (visible in FIG. 5 only), a post 118 that extends axially outwardly from the base 110, one or more flow apertures 122 extending through the base 110 and/or the post 118, and a flexible membrane 126 for restricting flow around the post 118, as will be discussed below. The valve 100 has an as-molded, somewhat planar, configuration as shown in FIGS. 1-6 wherein the flexible membrane 126 is located or rotated away from the post 118. The valve 100 must then be manipulated or folded in upon itself into a ready to dispense or non-dispensing, operative configuration where the flexible membrane 126 is located proximate to, or around, the post 118. In the non-dispensing configuration (FIGS. 7-12), the flexible membrane 126 is located laterally adjacent the post 118 to restrict or at least inhibit flow of a fluent substance through the valve 100 (i.e., through the annular area between the post 118 and the flexible membrane 126, as will be discussed in greater detail below).

The valve 100 can be forced to an "open" position or dispensing configuration when a sufficiently high-pressure differential acts across the opposite sides of the flexible membrane 126 to move it away (axially and/or radially) from the post 118 to create a flow path for a fluent substance.

Figure 2:
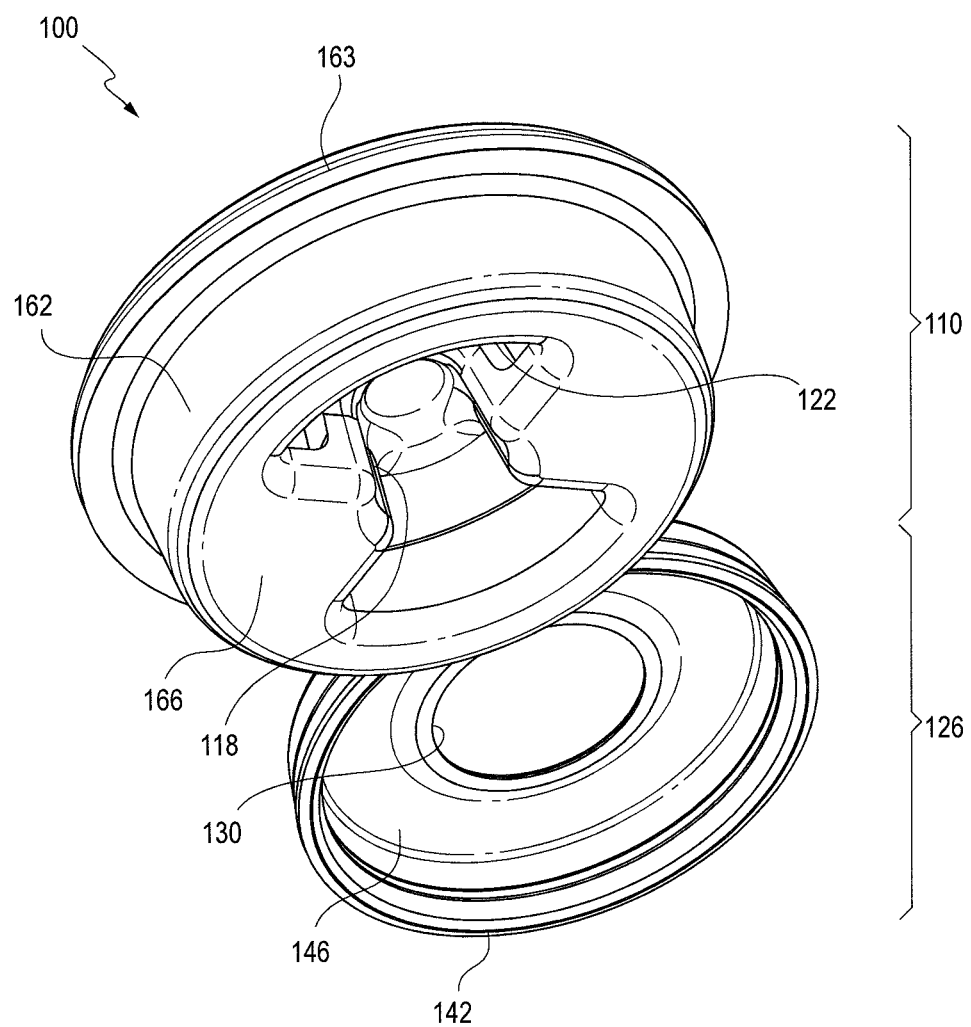
FIG. 2 is an enlarged, isometric view, taken from below, of the valve of FIG. 1.

Referring to FIGS. 1 and 2, the base 110 of the valve 100 is hollow and cuplike, wherein the post 118 extends axially outwardly from a recessed central portion of the base 110. A pair of diametrically opposing flow apertures 122 extend through the base 110 and the post 118 to permit flow of a fluent substance from a first side below the base 110 to a second side above the base 110. In one intended application, the first side (bottom) of the valve 100 faces the interior of a container of a fluent substance and the second side (top) faces an exterior, ambient environment. The flow apertures 122 have a kidney shaped or butterfly configuration and are arrange on diametrically opposite sides of the post 118. It will be understood that the base 110 may have only one aperture 122, or more than two apertures 122, which could be formed only in the recessed portion of the base 110 and not extend into the post 118. Furthermore, in some embodiments (not illustrated) the apertures 122 may be located in the outer, annular or cylindrical portion of the base 110 or only in the post 118.

Figure 3:
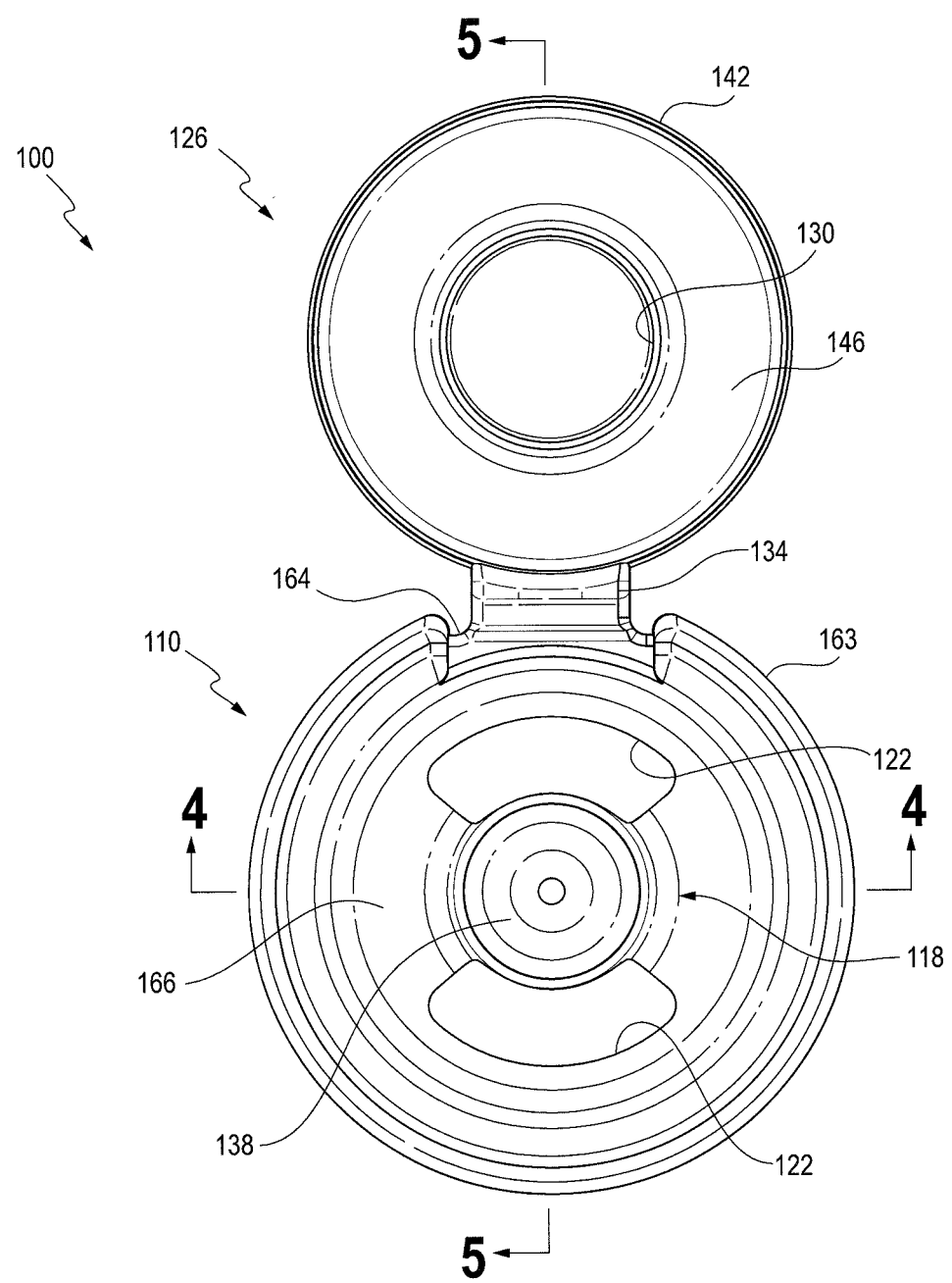
FIG. 3 is a top plan view of the valve of FIG. 1.

In the embodiment of the valve 100 illustrated in FIGS. 1-12, the post 118 is generally cylindrical in shape and terminates in a distal end 138 having a tapering, frustoconical cross-sectional shape, when viewed in a vertical plane containing the central axis 114 (e.g., FIGS. 4-5).

Referring to FIGS. 4 and 5, the base 110 defines a generally cylindrical outer wall 162 surrounding the post 118 and a transverse, inner wall 166 that extends laterally inwardly from the outer wall 162 to the post 118. A flange or annular retaining projection 163 extends laterally outwardly from the outer wall 162 for engaging a portion of a closure 200 or container (not illustrated) to secure the valve 100 at an opening thereof. The flange 163 includes a channel or cutout 164 (FIG. 1) to accommodate movement of the flexible membrane 126 relative to the base 110 when the valve 100 is placed in its non-dispensing, operative configuration.

Figure 6:
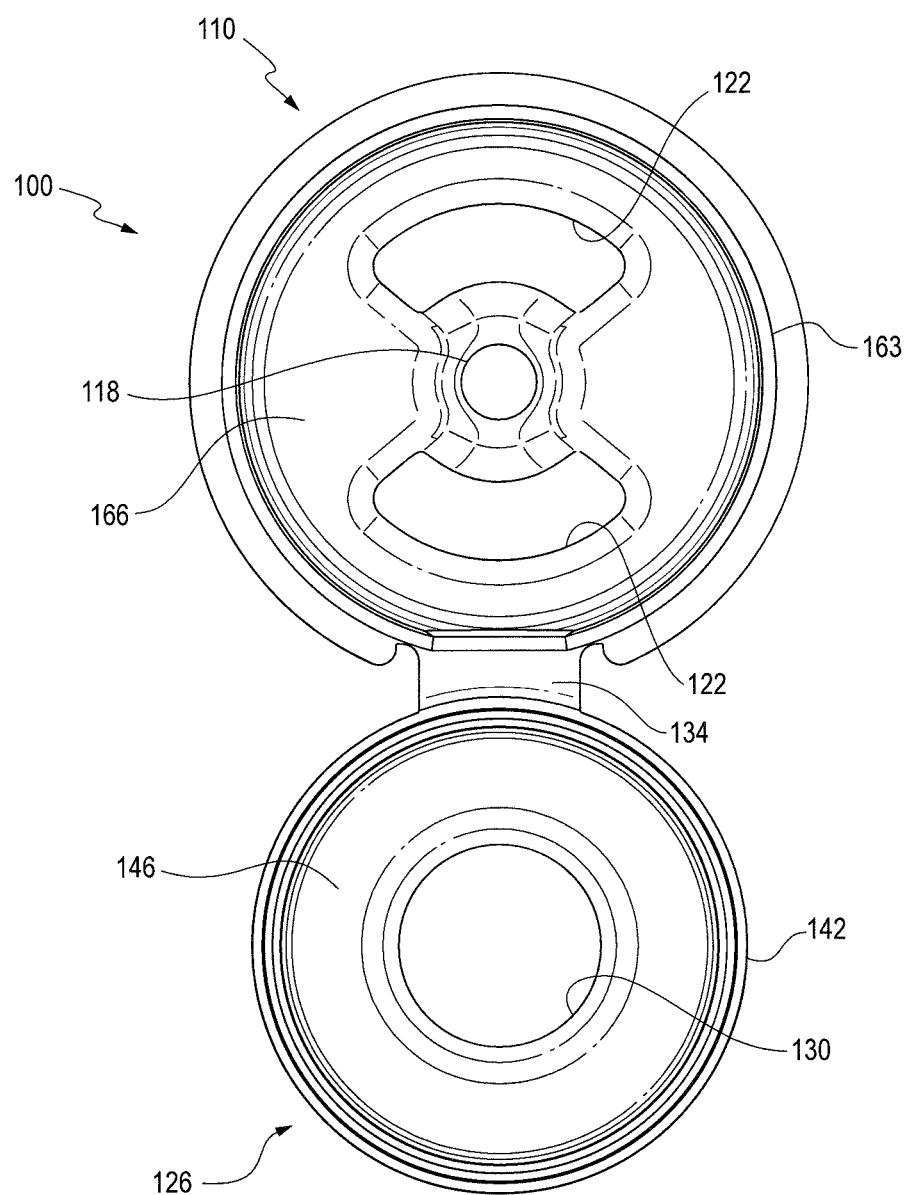
FIG. 6 is a bottom plan view of the valve of FIG. 1.
Figure 7:
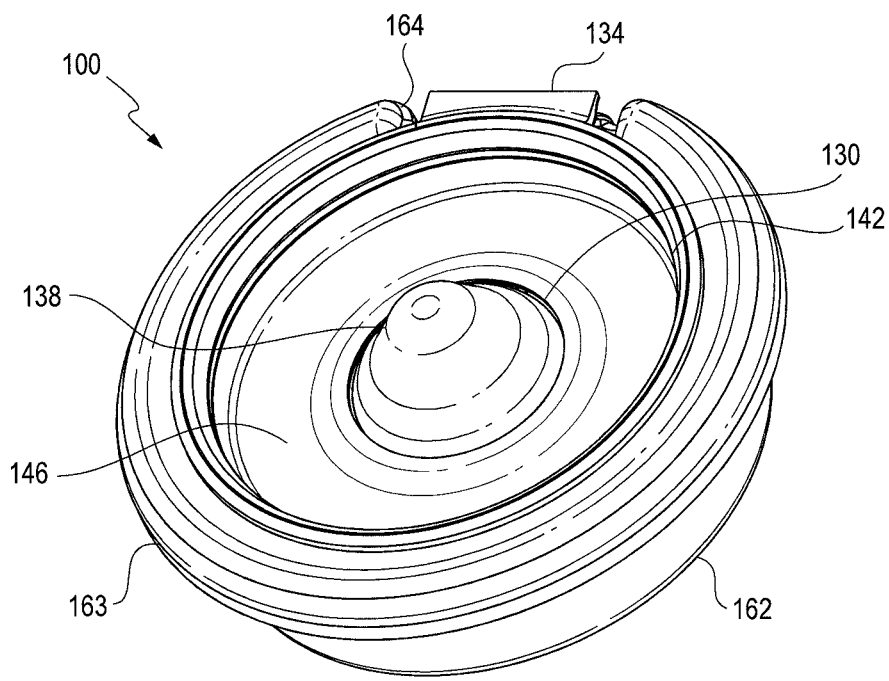
FIG. 7 is an enlarged, isometric view, taken from above, of the valve of FIG. 1 shows the valve rearranged or folded into an operative, ready to dispense configuration for being received within the opening of a container (not illustrated)
Figure 8:
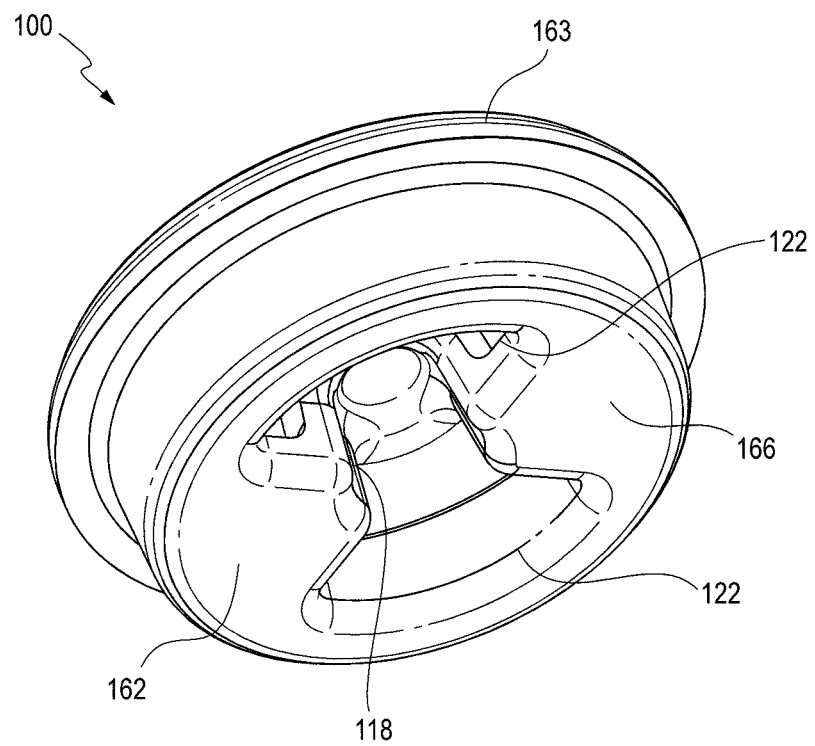
FIG. 8 is an enlarged, isometric view, taken from below, of the valve of FIG. 7.
Figure 9:
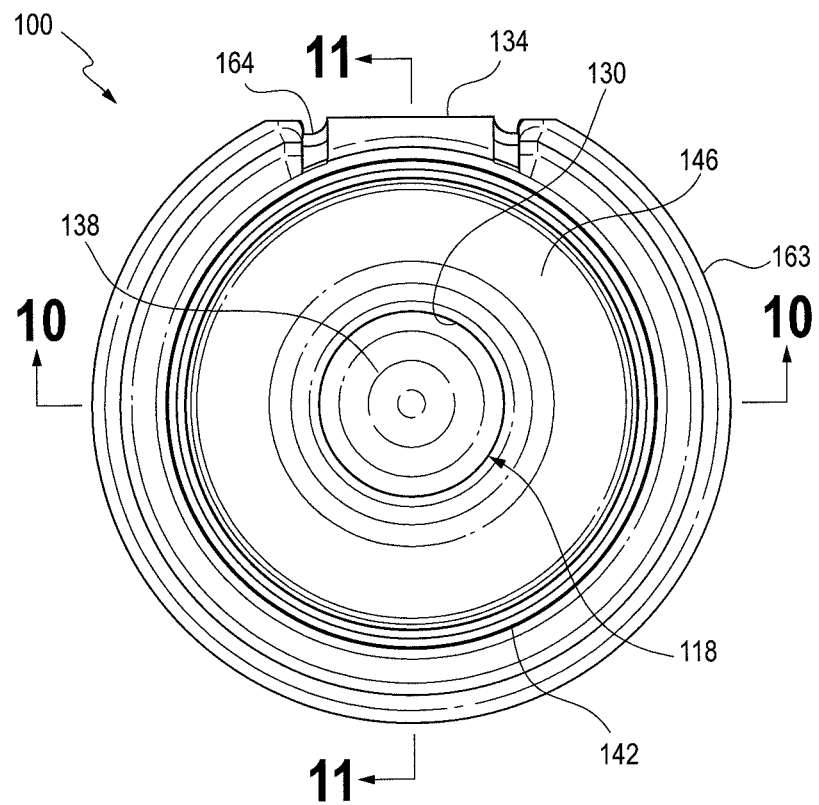
FIG. 9 is a top plan view of the valve of FIG. 7.

Referring to FIGS. 1, 3, and 6, the valve 100 includes a tether or hinge 134 connection between the base 110 and the flexible membrane 126. The hinge 134 is preferably a living hinge comprised of a relatively thin portion of material when the base 110 and flexible membrane 126 are a unitarily formed construction. As previously discussed, the valve 100 has a generally planar, as-molded configuration when manufactured as a unitary construction. The flexible membrane 126 can be rotated relative to the base 110 about the hinge 134 away from the generally planar, as-molded configuration into the operative, non-dispensing configuration so as to place an orifice 130 around or proximate to the post 118 (see, e.g., this configuration is shown in FIGS. 7-12). In some applications, it will be understood that the hinge 134 could be omitted. For example, the base 110 and the flexible membrane 126 could be formed separately and subsequently assembled by a force fit, clamping, adhesive, etc. Furthermore, the base 110 and the flexible membrane 126 could be bi-injection molded in the non-dispensing, operative configuration. Furthermore, any of the post 118, base 110, and/or membrane 126 could be formed together or could be comprised of any number of subcomponents.

In the first illustrated embodiment of the valve 100, the distal end 138 of the post 118 extends axially outwardly (beyond) the flexible membrane 126 in the aforementioned non-dispensing configuration. The flexible membrane 126 is also somewhat cup shaped and hollow, and it includes a peripheral wall or annular wall 142 for being nested within, and sealing against, a portion of the outer wall 162 of the base 110 with a friction fit in the aforementioned non-dispensing configuration. The flexible membrane 126 is further provided with a bottom or transverse wall 146 extending laterally inwardly of the peripheral wall 142. The transverse wall 146 terminates at, and defines, the orifice 130. While the orifice 130 is preferably a circular shape for receiving a cylindrical post 118, the orifice 130 may have other shapes depending on the shape of the post 118, such as polygonal, square, oval, or irregular, nonsymmetric shapes.

The peripheral wall 142 has a top end (axially outward end) and a bottom end (axially inward end) and the transverse wall 146 extends from the bottom end and is located axially inwardly of the top end with the flexible membrane 126 in its non-dispensing configuration surrounding the post 118. The transverse wall 146 of the valve 100 is substantially flat or planar.

In the presently preferred, illustrated embodiment of the valve 100, the flexible membrane 126 does not contact, and is spaced laterally from, an annular or lateral surface 119 of the post 118 with the flexible membrane 126 in the non-dispensing configuration.

The inventors have found that providing a valve 100 with a flexible membrane 126 which does not contact, and is spaced laterally from, a lateral surface 119 of the post 118 with the flexible membrane 126 in the non-dispensing configuration, may perform suitably for replacing prior art slit-type valves for a container or other system in which the valve 100 is installed. In particular, the improved valve 100 may eliminate the need for a retainer ring, adhesive, or other costly means for retaining the valve 100 at the opening of the closure or container, thus significantly reducing costs and manufacturing complexity of the valve and/or closure. The valve 100 may be used for relatively high viscosity fluent materials (e.g., ketchup, lotions, gels) to prevent or at least reduce or minimize, undesirable, premature valve opening events or other ingress or egress leakage events during transportation, storage, heating, or over-pressurization of the fluent substance container or system in which the valve 100 is installed. The inventors have further found that the arrangement of the flexible membrane 126 spaced laterally from the post 118 may permit beneficial in-venting into the container interior subsequent to dispensing a fluent substance through the valve 100 (where the membrane 126 moves into an inwardly deflected position or configuration).

It may be desirable to modify the valve 100 when used with relatively low viscosity fluent substances (e.g., juices, oils, liquid soaps, etc.) such that the flexible membrane 126 seals against or contacts the lateral surface 119 of the post 118 with the flexible membrane 126 in its non-dispensing configuration.

In still other configurations for relatively high viscosity fluent substances, the flexible membrane 126 could be configured to not contact, and be spaced axially outwardly from, the distal end 138 of the post 118 (rather than a lateral surface 119 of the post 118) with the flexible membrane 126 in its non-dispensing configuration. It may be desirable to modify the valve 100 in this configuration when used with relatively low viscosity fluent substances such that the flexible membrane 126 seals against or contacts the distal end 138 of the post 118 with the flexible membrane 126 in its non-dispensing configuration.

The flexible membrane 126, the flow apertures 122, and the spacing (or lack thereof) between the flexible membrane 126 and the post 118 of the valve 100 are preferably configured for use in conjunction with a particular fluent substance supply system or container, and a specific type of fluent substance, so as to achieve the flow characteristics desired. For example, the viscosity and density of the fluent substance are factors to be considered. The rigidity and durometer of the valve 100 material, and the size and thickness of the flexible membrane 126, are additional factors to be considered.

The valve 100 is flexible and it changes configuration under pressure between (1) a closed, rest position or non-dispensing configuration (e.g., FIG. 11), and (2) an open position or dispensing configuration. In the dispensing configuration, the flexible membrane 126 is moved slightly axially outwardly from its position proximate the post 118 in FIG. 11 to increase the cross-sectional area of the gap or annular space around the post 118 to permit a desired flow rate of fluent substance through the valve 100.

The fluent material within the container on which the valve 100 is installed may be said to be constrained or inhibited from moving axially outwardly beyond the flexible membrane 126 (for establishing communication through the valve 100) by the inherent rigidity of the membrane 126. The term "constrained" means that the fluent substance is substantially prevented by the flexible membrane 126 and post 118 interface from flowing, or at least any flowing greater than a predetermined leakage amount, when the valve 100 is subjected to an opening force or opening pressure differential that does not exceed a predetermined design value.

Figure 11:
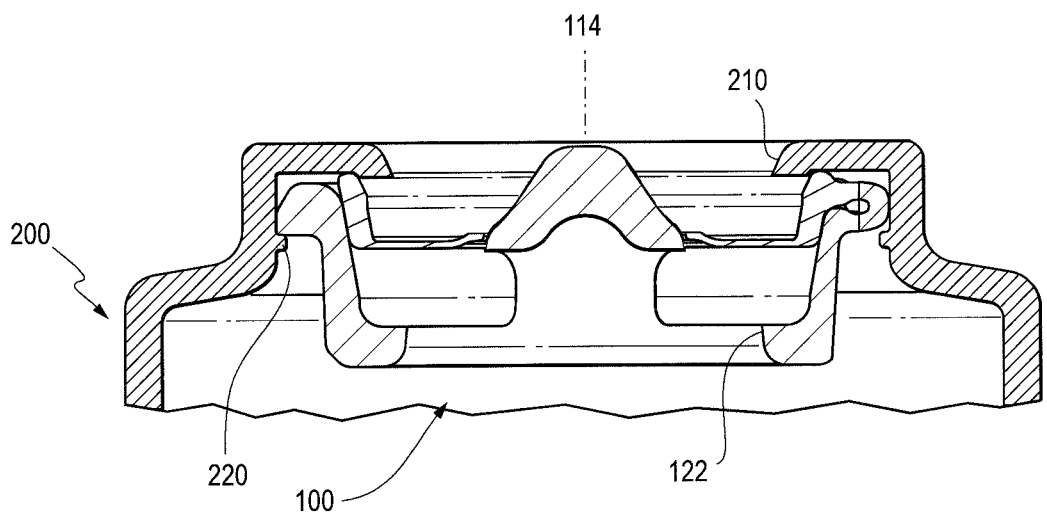
FIG. 11 is a cross-sectional view of the valve of FIG. 7, taken along view plane 11-11 in FIG. 9.
Figure 12:
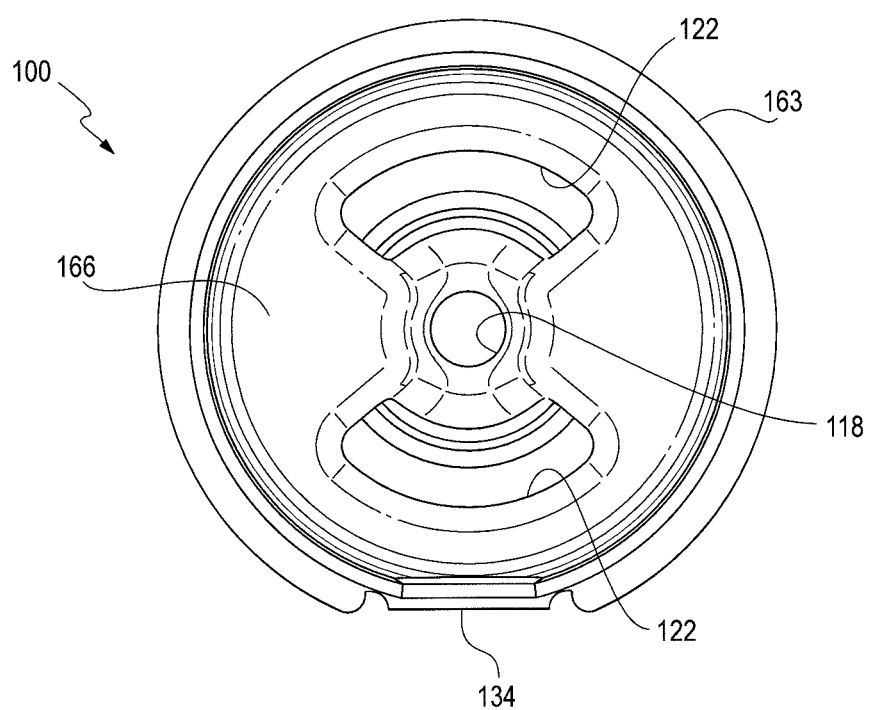
FIG. 12 is a bottom plan view of the valve of FIG. 7.

With reference to FIG. 11, the valve 100 is preferably arranged in a closure 200 at a location that is axially inward of an opening 210 of the closure 200. It will be understood that the valve 100 could be installed directly at the opening of a container (not illustrated) or other dispensing system.

A second embodiment of a valve according to the present invention is contemplated but is not illustrated. The second embodiment of the valve can be formed from the same material or materials that are discussed in detail above with respect to the first illustrated embodiment of the valve 100. The second embodiment of the valve has the same basic components of a body or base defining a central axis, a post that extends axially outwardly from the base, one or more flow apertures extending through the base and/or the post, and a flexible membrane. The second embodiment of the valve also has an as-molded, somewhat planar, configuration wherein the flexible membrane is located away from the post. The valve must then be manipulated or folded in upon itself into a ready to dispense or non-dispensing, operative configuration where the flexible membrane is located proximate to a lateral or annular side surface of the post. In the non-dispensing configuration, the flexible membrane is located adjacent the post to restrict or at least inhibit flow of a fluent substance through the valve.

The second embodiment of the valve can be forced to an "open" position or dispensing configuration when a sufficiently high-pressure differential acts across the opposite sides of the flexible membrane to move it away from the post to create a flow path for a fluent substance.

The second embodiment of the valve differs from the above-discussed first embodiment of the valve 100 in a number of respects. For example, the flow apertures of the second embodiment of the valve have the form of a pair of opposing, square-like slots in the base and the post.

Furthermore, in the second embodiment of the valve, the post is generally cylindrical in shape and terminates in a substantially flat distal end that terminates just beyond (axially outwardly) of the flexible membrane in its non-dispensing, operative configuration. The apertures are necessarily located beneath the flexible membrane in the non-dispensing configuration.

The base also defines a cylindrical outer wall surrounding the post and a transverse, inner wall that extends laterally inwardly from the outer wall to the connection of the post. A flange or annular retaining projection extends laterally outwardly from the outer wall for engaging a projection or portion of a closure or container to secure the valve at an opening thereof. The valve is preferably arranged in the closure at a location that is axially inward of an opening of the closure. The flange includes a channel or cutout to accommodate movement of the flexible membrane relative to the base when the valve is placed in its non-dispensing, operative configuration when rotated about a hinge.

In some applications, it will be understood that the hinge could be omitted. For example, the base and the flexible membrane could be formed separately and subsequently assembled by a force fit, clamping, adhesive, etc. Furthermore, the base and the flexible membrane could be bi-injection molded in the non-dispensing, operative configuration. Furthermore, any of the post, base, and/or membrane could be formed together or could be comprised of any number of subcomponents.

In the second contemplated embodiment of the valve, the flexible membrane is also somewhat cup shaped and hollow, and it includes a peripheral wall or annular wall for being nested within and sealing against a portion of the outer wall of the base with a friction fit in the aforementioned non-dispensing configuration. The flexible membrane and the base are each provided with an annular bead or beads for sealingly retaining the perimeter of the flexible membrane within the base. The transverse wall terminates at and defines the orifice. While the orifice is preferably a circular shape for receiving a cylindrical post, the orifice may have other shapes depending on the shape of the post, such as square, other polygonal, oval, or irregular, nonsymmetric shapes.

The peripheral wall has a top end (axially outward end) and a bottom end (axially inward end), and the transverse wall extends from the bottom end and is located axially inwardly of the top end with the flexible membrane in its non-dispensing configuration. The transverse wall of the second embodiment of the valve is planar and has a plurality of concentric annular ribs to assist and control the flexing or opening of the flexible membrane from its non-dispensing configuration into its dispensing configuration when subjected to a sufficiently high pressure differential.

In the second embodiment of the valve, the flexible membrane does not contact, and is just minimally spaced laterally from, the lateral surface of the post with the flexible membrane in the non-dispensing configuration.

It may be desirable to modify the second embodiment of the valve when used with relatively low viscosity fluent substances (e.g., juices, oils, liquid soaps, etc.) such that the flexible membrane seals against or contacts the lateral surface of the post with the flexible membrane in its non-dispensing configuration.

In still other configurations for relatively high viscosity fluent substances, the flexible membrane could be configured to not contact, and be spaced axially outwardly from, the distal end of the post with the flexible membrane in its non-dispensing configuration. It may be desirable to modify the valve in this configuration when used with relatively low viscosity fluent substances such that the flexible membrane seals against or contacts the distal end of the post with the flexible membrane in its non-dispensing configuration.

The flexible membrane, the flow apertures, and the spacing (or lack thereof) between the flexible membrane and the post of the valve are preferably configured for use in conjunction with a particular fluent substance supply system or container, and a specific type of fluent substance, so as to achieve the flow characteristics desired. For example, the viscosity and density of the fluent substance are factors to be considered. The rigidity and durometer of the valve material, and the size and thickness of the flexible membrane, are additional factors to be considered.

The second embodiment of the valve is flexible, and it changes configuration between (1) a closed, rest position or non-dispensing configuration, and (2) an open position or dispensing configuration. In the dispensing configuration, the flexible membrane is moved axially outwardly from its position proximate the post to increase the cross-sectional area of the gap around the post to permit a desired flow rate of fluent substance through the valve.

The fluent material within the container on which the valve is installed may be said to be constrained or inhibited from moving axially outwardly beyond the flexible membrane (for establishing communication through the valve) by the inherent rigidity of the membrane. The term "constrained" means that the fluent substance is substantially prevented by the flexible membrane and post interface from flowing, or at least any flowing greater than a predetermined leakage amount, when the valve is subjected to an opening force or opening pressure differential that does not exceed a predetermined design value.

It will be appreciated that while various theories and explanations have been set forth herein with respect to how the component configurations and arrangements may affect the operation of the inventive valve 100, there is no intention to be bound by such theories and explanations. Further it is intended that all structures falling within the scope of the appended claims are not to be otherwise excluded from the scope of the claims merely because the operation of such a valve may not be accounted for by the explanations and theories presented herein.

Various modifications and alterations to this invention will become apparent to those skilled in the art without departing from the scope and spirit of this invention. Illustrative embodiments and examples are provided as examples only and are not intended to limit the scope of the present invention.

What is claimed is:

1. A valve to permit selective communication therethrough, said valve comprising:
   a base defining a central axis;
   a post connected to said base;
   at least one flow aperture in said base and/or said post; and
   a flexible membrane having an orifice and having a non-dispensing configuration wherein said orifice is located proximate to said post to minimize communication through said valve, and said flexible membrane having a dispensing configuration wherein said orifice is moved away from said post for establishing communication through said valve, wherein said flexible membrane includes a peripheral wall for sealing against a portion of said base and a transverse wall extending inwardly of said peripheral wall and defining said orifice, and said peripheral wall defines a top end and a bottom end, wherein said transverse wall extends from said bottom end and is located axially inwardly of said top end with said flexible membrane in said non-dispensing configuration, relative to said central axis.

2. The valve according to claim 1 wherein said base and said flexible membrane are a unitary structure.

3. The valve according to claim 1 wherein said base and said post are a unitary structure.

4. The valve according to claim 1 wherein said base, said post, and said flexible membrane are a unitary structure.

5. The valve according to claim 1 wherein said base, said post, and said flexible membrane are an injection molded unitary structure formed from a thermoplastic elastomer.

6. The valve according to claim 1 wherein said base and said flexible membrane are connected by a hinge.

7. The valve according to claim 1 wherein said base and said flexible membrane are connected by a hinge and have a planar, as-molded configuration, and wherein said flexible membrane is configured to be rotated about said hinge away from said planar, as-molded configuration into said non-dispensing configuration such that said orifice is located around said post.

8. The valve according to claim 1 wherein said at least one flow aperture has the form of a pair of diametrically opposing flow apertures extending through each of said base and said post.

9. The valve according to claim 1 wherein said post is cylindrical and terminates in a distal end.

10. The valve according to claim 1 wherein said post includes a distal end that extends axially outwardly of said flexible membrane in said non-dispensing configuration, relative to said central axis.

11. The valve according to claim 1 wherein said post terminates in a distal end having a frustoconical cross-sectional shape, when viewed in a vertical plane containing said central axis.

12. The valve according to claim 1 wherein said post terminates in a flat distal end.

13. The valve according to claim 1 wherein said transverse wall is flat with said flexible membrane in said non-dispensing configuration.

14. The valve according to claim 1 wherein said base includes an outer wall surrounding said post and an inner wall extending laterally inwardly from said outer wall.

15. The valve according to claim 1 wherein said flexible membrane does not contact, and is spaced laterally from, a lateral surface of said post with said flexible membrane in said non-dispensing configuration.

16. The valve according to claim 1 wherein said flexible membrane seals against a lateral surface of said post with said flexible membrane in said non-dispensing configuration.

17. A valve to permit selective communication therethrough, said valve comprising:
   a base defining a central axis;
   a post connected to said base;
   at least one flow aperture in said base and/or said post; and
   a flexible membrane having an orifice and having a non-dispensing configuration wherein said orifice is located proximate to said post to minimize communication through said valve, and said flexible membrane having a dispensing configuration wherein said orifice is moved away from said post for establishing communication through said valve; wherein said flexible membrane does not contact, and is spaced axially outwardly from, a distal end of said post with said flexible membrane in said non-dispensing configuration.

18. The valve according to claim 1 wherein said flexible membrane seals axially against a distal end of said post with said flexible membrane in said non-dispensing configuration.

19. The valve according to claim 1 wherein said orifice of said flexible membrane is circular.

20. The valve according to claim 1 wherein said flexible membrane is resilient and configured to move from said dispensing configuration to said non-dispensing configuration when said flexible membrane is subjected to a pressure differential below a predetermined threshold.

21. The valve according to claim 1 wherein said base includes an outer wall surrounding said post, said outer wall includes a flange extending laterally outwardly therefrom.

22. A valve to permit selective communication therethrough, said valve comprising:
   a base defining a central axis;
   a post connected to said base;
   at least one flow aperture in said base and/or said post; and
   a flexible membrane having an orifice and having a non-dispensing configuration wherein said orifice is located proximate to said post to minimize communication through said valve, and said flexible membrane having a dispensing configuration wherein said orifice is moved away from said post for establishing communication through said valve; wherein said base includes an outer wall surrounding said post, said outer wall includes a flange extending laterally outwardly therefrom, said flange includes a channel to accommodate movement of said flexible membrane relative to said base.

23. The valve according to claim 1 in combination with a closure for a container, said valve arranged in said closure at a location that is axially inward of an opening of said closure.

24. The valve according to claim 1 in combination with a closure for a container, said valve including a flange extending laterally outwardly therefrom and said closure including at least one projection for engaging said flange to retain said valve.

* * * * *